(12) United States Patent  (10) Patent No.: US 7,921,716 B2
Morris Bamberg et al.  (45) Date of Patent: Apr. 12, 2011

(54) METHOD AND SYSTEM FOR MEASURING ENERGY EXPENDITURE AND FOOT INCLINE IN INDIVIDUALS

(75) Inventors: Stacy J. Morris Bamberg, Salt Lake City, UT (US); Mark A. Fehlberg, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 125 days.

(21) Appl. No.: 12/407,978

(22) Filed: Mar. 20, 2009

(65) Prior Publication Data

US 2009/0235739 A1 Sep. 24, 2009

Related U.S. Application Data

(60) Provisional application No. 61/070,413, filed on Mar. 20, 2008.

(51) Int. Cl.
*G01L 5/00* (2006.01)
(52) U.S. Cl. ............................................... 73/379.05
(58) Field of Classification Search .............. 73/379.05, 73/172; 725/9; 702/160; 455/3.01; 709/231; 600/587, 592
See application file for complete search history.

(56) References Cited

U.S. PATENT DOCUMENTS

| 4,745,930 | A | | 5/1988 | Confer |
| 5,033,291 | A | * | 7/1991 | Podoloff et al. ............. 73/172 |
| 5,323,650 | A | | 6/1994 | Fullen et al. |
| 5,408,873 | A | * | 4/1995 | Schmidt et al. .......... 73/862.625 |
| 5,437,289 | A | | 8/1995 | Liverance et al. |
| 5,471,405 | A | | 11/1995 | Marsh |
| 5,586,557 | A | | 12/1996 | Nelson et al. |
| 5,655,316 | A | | 8/1997 | Huang |
| 5,678,448 | A | * | 10/1997 | Fullen et al. ..................... 73/172 |
| 5,875,571 | A | | 3/1999 | Huang |
| 5,878,378 | A | | 3/1999 | Brommer et al. |
| 5,925,000 | A | | 7/1999 | Marciniak et al. |
| 5,929,332 | A | * | 7/1999 | Brown .......................... 73/172 |
| 6,018,705 | A | | 1/2000 | Gaudet et al. |
| 6,031,463 | A | | 2/2000 | Bechmann |
| 6,122,846 | A | | 9/2000 | Gray et al. |
| 6,186,000 | B1 | | 2/2001 | Kaneko et al. |
| 6,195,921 | B1 | | 3/2001 | Truong |
| 6,273,863 | B1 | | 8/2001 | Avni et al. |
| 6,360,597 | B1 | | 3/2002 | Hubbard, Jr. |
| 6,408,545 | B1 | | 6/2002 | Song |
| 6,611,789 | B1 | | 8/2003 | Darley |

(Continued)

FOREIGN PATENT DOCUMENTS

WO WO 2005/094679 10/2005

(Continued)

OTHER PUBLICATIONS

Morris Bamberg et al., U.S. Appl. No. 12/407,967, filed Mar. 20, 2009.

(Continued)

*Primary Examiner* — Jewel Thompson
(74) *Attorney, Agent, or Firm* — Thorpe North & Western LLP

(57) ABSTRACT

A method and system for measuring energy expenditure of individuals by measuring force from a plurality of foot-borne force sensitive resistors and calculating incline from a foot-borne tri-axial accelerometer.

13 Claims, 2 Drawing Sheets

U.S. PATENT DOCUMENTS

| | | | |
|---|---|---|---|
| 6,807,869 | B2 | 10/2004 | Farringdon et al. |
| 6,876,947 | B1 | 4/2005 | Darley et al. |
| 6,898,550 | B1 | 5/2005 | Blackadar et al. |
| 7,171,331 | B2 * | 1/2007 | Vock et al. .......... 702/160 |
| 7,191,644 | B2 | 3/2007 | Haselhurst et al. |
| 7,225,565 | B2 | 6/2007 | DiBenedetto et al. |
| 7,355,519 | B2 | 4/2008 | Grold et al. |
| 7,648,441 | B2 | 1/2010 | Silk |
| 2007/0202478 | A1 | 8/2007 | Al-Obaidi et al. |
| 2007/0204687 | A1 | 9/2007 | Haselhurst et al. |
| 2008/0108913 | A1 | 5/2008 | Lengsfeld et al. |

FOREIGN PATENT DOCUMENTS

| | | |
|---|---|---|
| WO | WO 2008/058048 | 5/2008 |

OTHER PUBLICATIONS

Harris-Love, Michelle et al., "Hemiparetic gait parameters in overground versus treadmill walking," Neurorehabilitation and Neural Repair, 2001, vol. 15, pp. 105-112.

Mattes, Sarah et al., "Walking symmetry and energy cost in persons with unilateral transtibial amputations: matching prosthetic and intact limb inertial properties," Arch Phys Med Rehabil. May 2000, vol. 81 pp. 561-568.

Novak, Peter, "Effect of step-synchronized vibration stimulation of soles on gait in parkinson's disease: a pilot study," May 4, 2006, Journal of NeuroEngineering and Rehabilitation, vol. 3, No, 9, 7 pages.

Mizelle, Chris et al., "Center of pressure measures predict hemiparetic gait velocity," ISB XXth Congress—ASB 29th Annual Meeting, Jul. 31-Aug. 5, Cleveland, Ohio, 1 page.

Kimmeskamp, S. et al., "Analysis of plantar pressures during gait of patients with parkinson's disease," Germany 2 pages.

Surdilovic, Dragoljub et al., "Gait phase and centre of pressure measuring system," IEEE, 2004, pp. 331-334.

Bamberg, Stacy J. Morris, "A shoe-integrated sensor system for wireless gait analysis and real-time therapeutic feedback," Jun. 2004, Thesis 314 pages.

Limits on the Measurement of Activity Level in Children Using Ultrasound and Photoelectric Cells, www.eric.ed.gov/ERICWebPortal/custom/portlets/recordDetails/detailmini.jsp?_nfpb=true... 1972, 2 pages.

Eaton, Warren, "Measuring Activity Level with Actometers: Reliability, Validity, and Arm Length" Child Development, 1983. 54, 720-726, (1 page).

Duncan, Michael, "Pedometer determined physical activity levels in primary school children from central England" Preventive Medicine, May 2007, vol. 44, Issue 5, pp. 416-420 (2 pages).

Urry, Stephen, "Plantar pressure-measurement sensors," Meas. Sci. Technol.,1999, 1 page abstract only.

Bamberg, Stacy J. Morris et al., "Gait analysis using a shoe-integrated wireless sensor system," IEEE, Transactions on Information Technology in Biomedicine, Jul. 2008, vol. 12, No. 4. pp. 413-423.

http://www.tgdaily.com, Gruener, Wolfgang, "MIT develops iShoe to keep you on your feet," Jul. 16, 2008, 1 page.

Trafton, Anne, "Balance problems? Step into the iShoe, MIT grad students' invention could one day prevent falls" Jul. 16, 2008, 2 pages.

Lindsay, Jay "Astronaut technology could prevent elderly falls insole sensors read how well a person is balancing, provide info to doctor," Jul. 31, 2008, 4 pages.

Perttunen, J.R. et al., "Gait asymmetry in patients with limb length discrepancy," Scand J. Med Sci Sports, 2004: vol. 14, pp. 49-56.

Perry, Stephen et al., "Efficacy and effectiveness of a balance-enhancing insole," Journal of Gerontology: Medical Sciences, vol. 63A, No. 6, pp. 595-602.

Granat, M.H. et al., "A body-worn gait analysis system for evaluating hemiplegic gait," 1995, Med. Eng. Phys. vol. 17, No. 5, pp. 390-394.

Ming-Yih Lee et al., "Design of a new biofeedback proprioceptive neuromuscular facilitation system for below-knee amputees," Biomed Engineering Applications, basis and communications, 2006, vol. 18, No. 4. pp. 109-197.

Rodgers, Mary et al., "Effects of gait velocity on COP symmetry measures in individuals with stroke," http://pt.umaryland.edu, 2 pages.

Roberts, Dawn E., "Measurement of physical activity with accelerometers in children," 2007, Scholarworks@UMass Amherst, http://scholarworks.umass.edu/dissertations/AAI3254924/, abstract only.

Tryon Warren, "Measuring activity using actometers: A methodological study," Journal of Psychopathology and Behavioral Assessment, Jun. 1984, vol. 6. No. 2 abstract only.

Jelen Piotr et al., "Expressing gait-line symmetry in able-bodied gait," Dynamic Medicine, BioMed Central, Dec. 19, 2008, 9 pages.

Bamberg, et al., "Toward In-shoe motion analysis and activity monitoring: Detecting incline during walking gait," 1 page.

Zhang, Kuan et al., "Assessment of human locomotion by using an insole measurement system and artificial neural networks," Journal of Biomechanics, 2005, 38 pages 2276-2287.

Bamberg et al., "Toward in-shoe motion analysis and activity monitoring: detecting incline during walking gait," poster, BMES conference, Sep. 27, 2007, 1 page.

Bamberg et al., "An interactive auditory feedback system to improve gait symmetry in presons with amuputations," 1 page.

Paradiso, Joseph et al., "Interactive therapy with instrumented footwear," Apr. 24-29, 2004, Vienna Austria, 3 pages.

Bamberg, Stacy J. Morris et al., "Development of a quantitative in-shoe measurement system for assessing balanc: sixteen-sensor insoles," IEEE, EMBS Annual International Conference, Aug. 30, 2006-Sep. 3, 2006.

* cited by examiner

METHOD AND SYSTEM FOR MEASURING ENERGY EXPENDITURE AND FOOT INCLINE IN INDIVIDUALS

PRIORITY CLAIM

Priority is claimed to U.S. Provisional Patent Application Ser. No. 61/070,413, filed Mar. 20, 2008, which is hereby incorporated herein by reference in its entirety.

BACKGROUND

1. Field of the Invention

The present invention relates generally to activity monitoring, foot inclination, and estimation of energy expenditure of an individual.

2. Related Art

An inactive lifestyle is often seen in our children, especially beginning in 9-14 year-olds. Behavior patterns often begin in this age-group and track into adulthood. Lack of physical activity affects early onset diabetes, obesity, heart disease, and other chronic illnesses. These illnesses have a negative effect on a child's quality-of-life and functional status, and increase parent burden.

Physical inactivity is an important, modifiable lifestyle factor that is an essential factor in energy balance, and thus key in obesity prevention and treatment. Physical inactivity also contributes to risk for increased morbidity and mortality of other chronic conditions, and is an independent risk factor for cardiovascular disease, the leading cause of death in the United States. There is a well-documented trend of increasing sedentary activity for all ages in the United States and recommendations for increasing physical activity. What is known about children's physical activity is that: (a) physical activity begins to decline in the 9-14 year age group, especially for girls, (b) patterns of activity tend to track from childhood into adulthood; and (c) inactivity is related to increased risk for morbidity of chronic conditions. However, recommendations for assessment, health promotion, and intervention are difficult to implement and evaluate, challenged by the lack of adequate screening and measurement tools that are cost-effective, efficient, easily usable, reliable and valid. Appropriate, reliable and valid screening and measurement tools are critical if clinicians and researchers working with children are to fully understand activity or lack thereof, and if we are to fully explicate the component of activity/inactivity as a contributing factor in obesity and other conditions in children.

Self-report physical activity provides adequate and reliable data, but validity data vary widely and are inconsistent. Motion monitors are considered more objective, less burdensome, and less invasive than other measurement techniques. However, current motion monitors involve high monetary expense and use burden. Additionally, current devices are difficult to stabilize on the waistband, especially for large-waisted children whose girth adversely effects placement and diminishes measurement accuracy. Furthermore, activity on an incline, force distribution under the foot, and inverted activities (i.e. playground activities) have not been able to be efficiently measured.

SUMMARY OF THE INVENTION

The inventors of the present invention have recognized that it would be advantageous to develop a method and system for measuring energy expenditure of individuals, such as children with inactive behavior patterns that affect early onset diabetes, obesity, heart disease and other chronic illnesses, by measuring force from a plurality of foot-borne force sensitive resistors and calculating incline from a foot-borne tri-axial accelerometer. In addition, the inventors of the present invention have recognized that it would be advantageous to develop a method and device for integrating cost effective, efficient, and less burdensome measurement tools that help to better understand children's physical activity, provide a more substantial foundation for intervention and monitoring, and improve overall clinical utility. Additionally, the inventors of the present invention have recognized that it would be advantageous to develop a method and device having an innovative and inexpensive, motion tracker developed to maximize available technology in motion-monitored physical activity measurement.

The invention provides a method for analyzing motion of an individual. At least a tri-axial accelerometer is affixed with respect to a user's foot. Accelerometer data is collected from the tri-axial accelerometer. Incline during stance phase is determined based on the accelerometer data from the tri-axial accelerometer using an electronic processor.

In accordance with one aspect of the present invention, energy expenditure of the individual can be determined based on the accelerometer data using the electronic processor.

In accordance with another aspect of the present invention, stance phase can be determined by using force sensitive resistors. A plurality of force sensitive resistors can be affixed with respect to the user's foot. Force data from the plurality of force sensitive resistors is collected. Stance phase is determined based on the force data from the plurality of force sensitive resistors using the electronic processor.

In accordance with another aspect of the present invention, stance phase can be determined by using the tri-axial accelerometer.

The invention also provides a method for measuring activity in an individual. Data is collected from a multi-sensor insole disposed in a shoe, including force data from a plurality of force sensitive resistors and accelerometer data from a tri-axial accelerometer. The data from the sensors of the multi-sensor insole is determined with an electronic processor to determine the energy expenditure of the individual based on the force data and inclination of the shoe with respect to the ground during stance phase over a period of time. In accordance with one aspect of the present invention, different types of activities can be identified using pattern recognition.

The present invention also provides a foot-worn, in-shoe based sensor system configured to measure activity in a wearer of a shoe configured to be donned on a user's foot. A sensor array is associated with the shoe, including a plurality of force sensitive resistors and a tri-axial accelerometer. An electronic processor is operably coupled to the sensor array to receive data from the sensor array and analyzing the data to determine an activity level of the user based on a determined inclination of the shoe during stance phase.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

Figure 1:
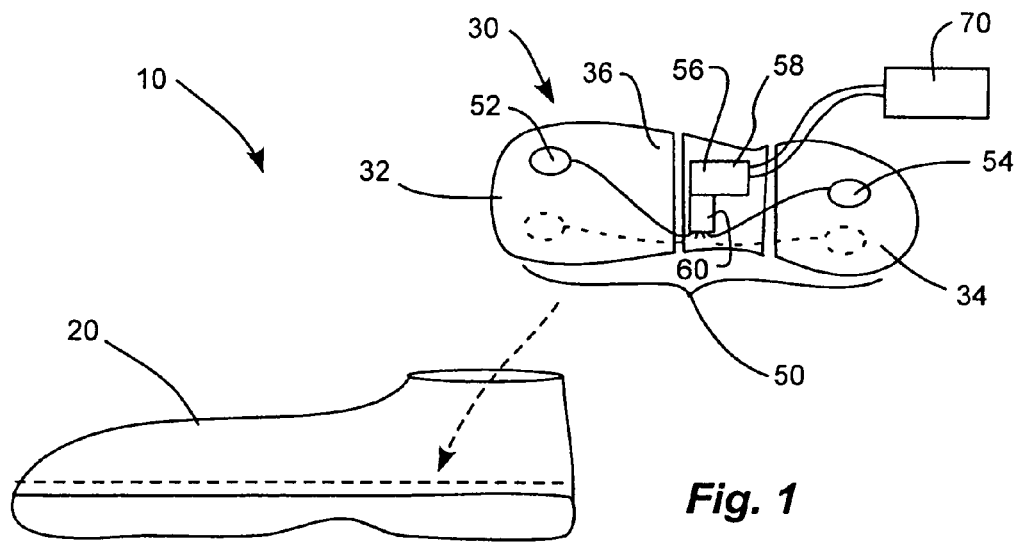
FIG. 1 is a schematic view of a shoe with a multi-sensor insole in accordance with an embodiment of the present invention.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

The embodiments of the present invention described herein provide for an inexpensive, foot-worn monitor that includes incline in activity measurement to provide improved assessment of physical activity of the foot-worn monitor. In one aspect, the foot-worn monitor can include a shoe or pair of shoes with multi-sensor insoles that include force sensors and accelerometers in order to determine incline and/or orientation of the shoe during gaited motion. The terms "shoe" or "shoes" are used broadly herein to mean any footwear, whether commercially available or custom made for carrying the sensors, such as shoe, sneaker, boot, sandal, slipper, athletic footwear, sock, etc. More specifically, the insole can include a plurality of force sensitive resistors in the heel and toe of the insole, and a tri-axial accelerometer in an arch section of the insole. The insole can be formed of a polymeric material such as silicone. In use, an individual can wear the insole in the shoe, and the orientation with respect to the earth's gravitational field of the surface traversed by the shoe can be determined using the sensors in the insole. The force sensors can determine when the shoe is flat on the ground and thus also provide the step count.

As illustrated in FIG. 1, a foot-worn activity monitor, indicated generally at 10, in accordance with the present invention is shown for use in measuring activity in a wearer of the shoe. The activity monitor 10 can include a shoe 20, an insole, indicated generally at 30, a sensor array, indicated generally at 50, associated with the insole, and an electronic processor, indicated generally at 70, operably coupled to the sensor array.

The shoe 20 can be an ordinary shoe or boot as known in the art. For example, the shoe 20 can be a sneaker or dress shoe that can be donned on a natural foot or a prosthetic foot of the user. The shoe 20 can be part of a pair of shoes and both shoes can include the foot worn activity monitor described herein.

The insole 30 can be sized and shaped to fit within the shoe. The insole 30 can be formed of an elastomeric and/or polymeric material such as rubberized silicone. The insole 30 can have a toe section 32, a heel section 34, and an arch section 36 disposed between the toe section and heel section.

The sensor array 50 can be associated with the insole 30. The sensor array 50 can measure the incline or orientation of the shoe, and the force applied to the shoe during motion or activity of the user. In one aspect, the sensors of the sensor array 50 can be imbedded in the elastomeric and/or polymeric material of the insole 30. The sensor array 50 can be attached externally to the shoe, for instance fastened to the shoelaces or attached to another surface of the shoe.

The sensor array 50 can include an accelerometer, a two-axis accelerometer, a tri-axial accelerometer, a force sensor, a strain gage, a level, a force sensitive resistor, a pressure sensor, a pressure sensing array, and the like. For example, in one aspect, the sensor array 50 can include one or more force sensitive resistors 52 placed underneath the toe section 32 of the insole 30, and one or more force sensitive resistors 54 placed underneath the heel section 34 of the insole. Additionally, the sensor array can include a tri-axial accelerometer 56 placed underneath the arch section 36 of the insole. In this way, the sensor array 50 can sense the forces applied to the shoe, the step count of the shoe, and the inclination or orientation of the shoe with respect to level or the gravitational field of the earth.

In accordance with one aspect of the invention, the insole 30 can be segmented into a plurality of parts or pieces to fit within different size shoes and accommodate different sized feet. For example, the insole can include the toe piece 32, the heel piece 34, and the middle piece or arch section 36 which can be connected but movable with respect to one another. The toe piece can include the one or more force sensitive resistors 52 and can be positioned at a toe of the shoe. The heel piece 34 can include the one or more force sensitive resistors 54 and can be positioned at a heel of the shoe. The middle piece 36 can include the tri-axial accelerometer 56 and/or circuits.

Additionally, the sensor array can include electronic circuitry in communication with the sensors 52, 54 and 56 to route the sensor data to the electronic processor 70. For example, the circuitry can include a primary circuit board 58 with the tri-axial accelerometer and a multiplexer, and a secondary circuit board 60 operatively coupled to the primary circuit board with connections for the force sensitive resistors, a voltage divider coupled to an op-amp buffer, and a multiplexer.

The electronic processor 70 can be operably coupled to the sensor array 50 to receive data from the sensors of the sensor array. The electronic processor 70 can analyze the data to determine an activity level of the user. The electronic processor can include a microprocessor, a microcomputer, a computer, and the like. In this way, the electronic processor 70 can analyze data from the force sensors and tri-axial accelerometer to determine the energy expenditure of an individual wearing the shoe based on the force applied to the shoe and the orientation of the shoe with respect to the ground over a period of time.

Figure 2:
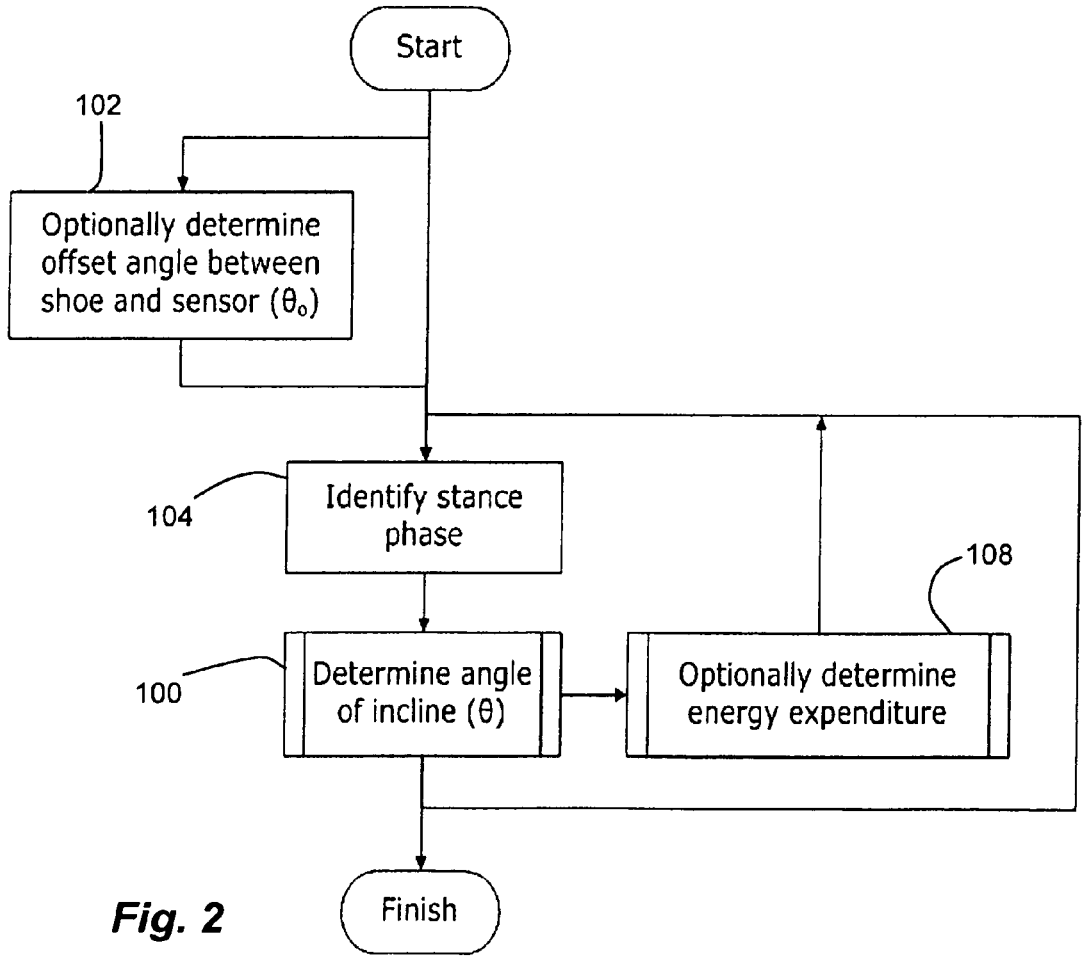
FIG. 2 is a flow chart of a method for determining incline of a foot or shoe, and a method of determining energy expenditure of an individual in accordance with an embodiment of the present invention.

The present invention also provides for a method for analyzing motion, and/or shoe inclination during motion, of an individual, and for method for measuring activity in the individual. At least a tri-axial accelerometer is affixed with respect to a user's foot. The tri-axial accelerometer can be affixed to a shoe. For example, the accelerometer can be part of an insole disposed in the shoe, such as at an arch section or middle piece of the insole. Alternatively, the accelerometer can be in a separate enclosure that is tied to the shoelaces or affixed externally to the shoe. Accelerometer data is collected from the tri-axial accelerometer. Incline during stance phase is determined 100 (FIG. 2) based on the accelerometer data from the tri-axial accelerometer using an electronic processor.

Incline can be estimated utilizing the equation (1):

$$\theta = \sin^{-1}\left(\frac{A_x + A_y}{\sqrt{2(A_x^2 + A_y^2 + A_z^2)}}\right) \quad (1)$$

where $A_x$, $A_y$ and $A_z$ are magnitudes of acceleration measured by the tri-axial accelerometer in x, y and z directions, respectively, and $\theta$ is the angle of incline.

Offset between the shoe and the sensor board when the system is initialized and the foot is on level ground can be determined 102 (FIG. 2) utilizing the equation (2):

$$\theta_o = \sin^{-1}\left(\frac{A_{x_o} + A_{y_o}}{\sqrt{2(A_{x_o}^2 + A_{y_o}^2 + A_{z_o}^2)}}\right) \quad (2)$$

where $A_{xo}$, $A_{yo}$ and $A_{zo}$ are magnitudes of acceleration measured by the tri-axial accelerometer in x, y and z directions, respectively, measured when the foot is initially flat on level ground, and $\theta_o$ is the offset angle between the shoe and the sensor board.

Figure 3A:
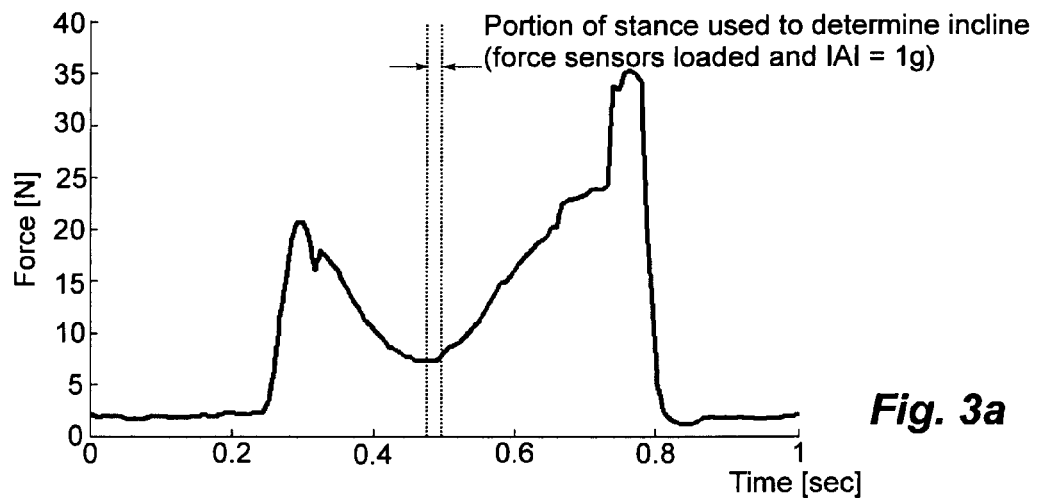
FIG. 3a is an exemplary graph of force vs. time for the sum of the force sensor outputs showing a portion of stance used to determine incline.
Figure 3B:
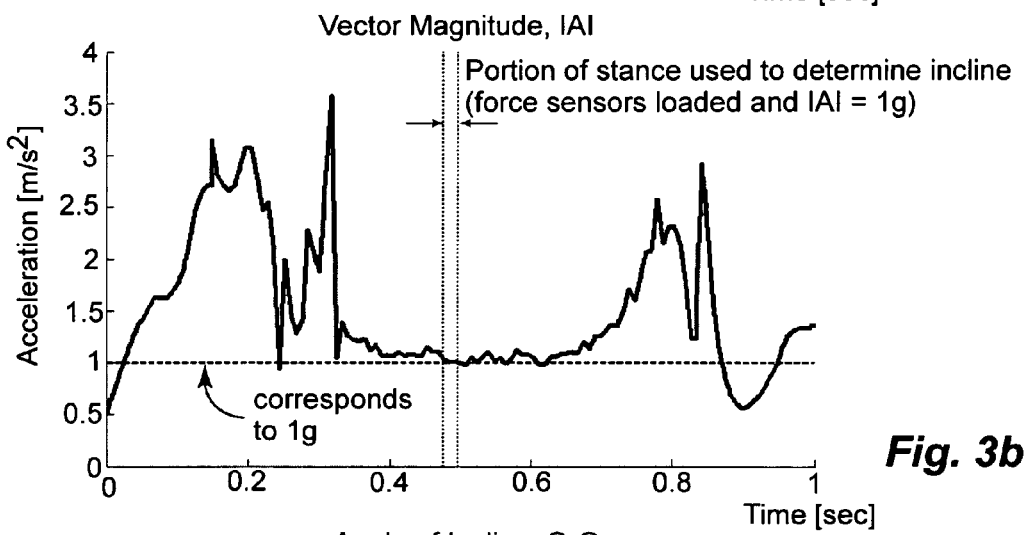
FIG. 3b is an exemplary graph of acceleration vs. time for the vector magnitude showing a portion of stance used to determine incline.
Figure 3C:
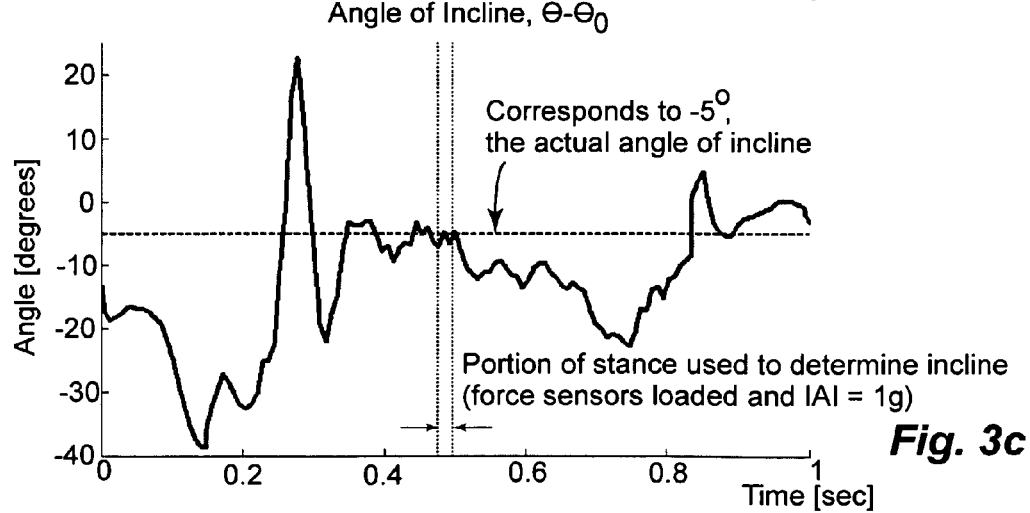
FIG. 3c is an exemplary graph of angle vs. time showing an incline at the portion of stance used to determine incline in FIGS. 3a and 3b.

Incline during gait can be determined 100 (FIG. 2) utilizing the equation (3):

$$\theta = \sin^{-1}\left(\frac{A_x + A_y}{\sqrt{2(A_x^2 + A_y^2 + A_z^2)}}\right) - \theta_o \quad (3)$$

where $A_x$, $A_y$ and $A_z$ are magnitudes of acceleration measured by the tri-axial accelerometer in x, y and z directions, respectively, measured when the foot is in stance phase, and $\theta$ is the angle of incline. An example of determining incline is shown in FIG. 3c. The angle can be determined during stance phase, examples of which are shown in FIGS. 3a and 3b.

Stance phase can be determined 104 (FIG. 2) based on the accelerometer data from the tri-axial accelerometer using the electronic processor. A magnitude of acceleration vector can be determined utilizing the equation (4):

$$|\vec{A}| = \sqrt{A_x^2 + A_y^2 + A_z^2} \quad (4)$$

where $A_x$, $A_y$ and $A_z$ are magnitudes of acceleration measured by the tri-axial accelerometer in x, y and z directions, and A is the magnitude of the acceleration vector. When the foot is flat on the floor, the magnitude of total acceleration should be substantially equal to 1 g during stance phase. An example of the acceleration data measured from the accelerometer is shown in FIG. 3b. Also shown is the determination of stance phase.

The energy expenditure of the individual can be determined 108 (FIG. 2) based on the accelerometer data from the tri-axial accelerometer using the electronic processor.

Alternatively, stance phase can be determined 104 (FIG. 2) utilizing a plurality of force sensitive resistors affixed with respect to the user's foot. Again, the plurality of force sensitive resistors can be affixed to a shoe. For example, the force sensitive resistors can be part of an insole disposed in the shoe, such as at toe and heel pieces of the insole. Force data can be collected from the plurality of force sensitive resistors.

Stance phase can be determined 104 (FIG. 2) based on the force data from the plurality of force sensitive resistors using the electronic processor. An example of the force data measured from the force sensitive resistors is shown in FIG. 3a. Also shown is the determination of stance phase.

The energy expenditure of the individual can be determined 108 (FIG. 2) based on the force data and the inclination of the shoe with respect to the ground over a period of time using the electronic processor. For example, energy expenditures of activities such as walking and running can be quantified based on the individual's speed, and energy expenditures are known to increase while going uphill and decrease while going downhill. The speed of the individual can be determined from the step rate multiplied by the step length (or stride rate multiplied by stride length), and then adjusted accordingly if the surface is not level. For instance, this could be done using a lookup table (with interpolation if necessary) using published energy expenditures given the incline of the surface, or an appropriate multiplication factor could be applied to a standard calculation of energy expenditure (e.g. calories burned) on a level surface. In addition, information from force sensors can be used to further refine the determination of energy expenditure. Thus, the energy expenditure can be determined based on the rate of steps, the step length (or stride rate and stride length), and the inclination of the shoe with respect to the ground during stance phase over a period of time. Similarly, pattern recognition can be used to identify specific activities (e.g. swinging on playground swings, hopping on one foot, etc.) to use known energy expenditures.

Affixing the accelerometer and the force sensitive resistors can include positioning a toe piece of an insole with at least one force sensitive resistor at a toe of the shoe; positioning a heel piece of the insole with at least one force sensitive resistor at a heel of the shoe; positioning a middle piece of the insole with the tri-axial accelerometer in the shoe between the toe and heel pieces; positioning an insole with at least one force sensitive resistor and the accelerometer outside of the shoe.

A method for making a shoe that measures the activity level of the wearer of the shoe includes preparing a mold of an insole of the shoe. An insole can be formed by adding an uncured polymeric material to the mold and allowing it to cure. A plurality of force sensitive resistors can be placed in the toe and heel of the mold or insole. A tri-axial accelerometer can be placed in the arch section of the mold or insole. The plurality of force sensitive resistors and the tri-axial accelerometer can be coupled to an electronic processor to determine the energy expenditure of an individual wearing the shoe based on the force applied to the shoe and the inclination of the shoe with respect to the ground over a period of time. The cured insole along with the sensors can be placed into the shoe.

The tri-axial accelerometer can be enclosed within a small housing with the electronic processor, and can be affixed externally to the shoe. It can be tied to the laces of the shoe, or clipped to the heel of the shoe, or another surface of the shoe.

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth herein.

The invention claimed is:

1. A method for analyzing motion of an individual, comprising:
   a) affixing at least a tri-axial accelerometer with respect to a user's foot;
   b) collecting accelerometer data from the tri-axial accelerometer;
   c) determining incline during stance phase based on the accelerometer data from the tri-axial accelerometer using an electronic processor;
   d) determining stance phase based on the accelerometer data from tri-axial accelerometer using the electronic processor; and
   e) determining an energy expenditure of the individual based on the inclination of the shoe with respect to the ground over a period of time using the electronic processor.

2. A method in accordance with claim 1, further comprising:
   determining energy expenditure of the individual based on the accelerometer data from the tri-axial accelerometer using the electronic processor.

3. A method in accordance with claim 1, further comprising:
   affixing a plurality of force sensitive resistors with respect to the user's foot;
   collecting force data from the plurality of force sensitive resistors; and
   determining stance phase based on the force data from the plurality of force sensitive resistors using the electronic processor.

4. A method in accordance with claim 3, further comprising:
   determining an energy expenditure of the individual based on the force applied to the shoe and the inclination of the shoe with respect to the ground over a period of time using the electronic processor.

5. A method in accordance with claim 1, wherein determining stance phase further includes determining a magnitude of acceleration vector utilizing the equation:

$$|\vec{A}| = \sqrt{A_x^2 + A_y^2 + A_z^2}$$

where $A_x$, $A_y$ and $A_z$ are magnitudes of acceleration measured by the tri-axial accelerometer in x, y and z directions, and A is the magnitude of the acceleration vector; and wherein the magnitude of total acceleration being substantially equal to 1 g during stance phase.

6. A method in accordance with claim 1, further comprising:
   estimating incline utilizing the equation:

$$\theta = \sin^{-1}\left(\frac{A_x + A_y}{\sqrt{2(A_x^2 + A_y^2 + A_z^2)}}\right)$$

where $A_x$, $A_y$ and $A_z$ are magnitudes of acceleration measured by the tri-axial accelerometer in x, y and z directions, respectively, and $\theta$ is the angle on incline.

7. A method in accordance with claim 1, further comprising:
   determining offset between the shoe and the sensor board when the system is initialized and the foot is on level ground utilizing the equation:

$$\theta_o = \sin^{-1}\left(\frac{A_{x_o} + A_{y_o}}{\sqrt{2(A_{x_o}^2 + A_{y_o}^2 + A_{z_o}^2)}}\right)$$

where $A_{xo}$, $A_{yo}$ and $A_{zo}$ are magnitudes of acceleration measured by the tri-axial accelerometer in x, y and z directions, respectively, measured when the foot is initially flat on level ground, and $\theta_o$ is the offset angle between the shoe and the sensor board; and
   determining incline during gait utilizing the equation:

$$\theta = \sin^{-1}\left(\frac{A_x + A_y}{\sqrt{2(A_x^2 + A_y^2 + A_z^2)}}\right) - \theta_o$$

where $A_x$, $A_y$ and $A_z$ are magnitudes of acceleration measured by the tri-axial accelerometer in x, y and z directions, respectively, measured when the foot is in stance phase, and $\theta$ is the angle of incline.

8. A method in accordance with claim 1, further comprising:
   positioning a toe piece of an insole with at least one force sensitive resistor at a toe of the shoe;
   positioning a heel piece of the insole with at least one force sensitive resistor at a heel of the shoe; and
   positioning a middle piece of the insole with the tri-axial accelerometer in the shoe between the toe and heel pieces.

9. A method for measuring activity in an individual, comprising:
   a) collecting data from a multi-sensor insole disposed in a shoe, including force data from a plurality of force sensitive resistors and accelerometer data from a tri-axial accelerometer;
   b) analyzing the data from the sensors of the multi-sensor insole with an electronic processor to determine the energy expenditure of the individual based on the force data and inclination of the shoe with respect to the ground during stance phase over a period of time; and
   c) determining stance phase based on the force data from the plurality of force sensitive resistors using the electronic processor.

10. A method in accordance with claim 9, further comprising:
    estimating the inclination utilizing the equation:

$$\theta = \sin^{-1}\left(\frac{A_x + A_y}{\sqrt{2(A_x^2 + A_y^2 + A_z^2)}}\right)$$

where $A_x$, $A_y$ and $A_z$ are magnitudes of acceleration measured by the tri-axial accelerometer in x, y and z directions, respectively, and $\theta$ is the angle of inclination.

11. A method in accordance with claim 9, further comprising:
    determining offset between the shoe and the sensor board when the system is initialized and the foot is on level ground utilizing the equation:

$$\theta_o = \sin^{-1}\left(\frac{A_{x_o} + A_{y_o}}{\sqrt{2(A_{x_o}^2 + A_{y_o}^2 + A_{z_o}^2)}}\right)$$

where $A_{xo}$, $A_{yo}$ and $A_{zo}$ are magnitudes of acceleration measured by the tri-axial accelerometer in x, y and z directions, respectively, measured when the foot is initially flat on level ground, and $\theta_o$ is the offset angle between the shoe and the sensor board; and determining incline during gait utilizing the equation:

$$\theta = \sin^{-1}\left(\frac{A_x + A_y}{\sqrt{2(A_x^2 + A_y^2 + A_z^2)}}\right) - \theta_o$$

where $A_x$, $A_y$ and $A_z$ are magnitudes of acceleration measured by the tri-axial accelerometer in x, y and z directions, respectively, measured when the foot is in stance phase, and $\theta$ is the angle of incline.

12. A method in accordance with claim 9, further comprising:
  determining stance phase based on the force data and the accelerometer data and utilizing the equations:

$$|\vec{A}| = \sqrt{A_x^2 + A_y^2 + A_z^2}$$

where $A_x$, $A_y$ and $A_z$ are magnitudes of acceleration measured by the tri-axial accelerometer in x, y and z directions, and A is the magnitude of the acceleration vector; and wherein the magnitude of total acceleration being substantially equal to 1 g during stance phase.

13. A method in accordance with claim 12, further comprising:
  positioning a toe piece of an insole with at least one force sensitive resistor at a toe of the shoe;
  positioning a heel piece of the insole with at least one force sensitive resistor at a heel of the shoe; and
  positioning a middle piece of the insole with the tri-axial accelerometer in the shoe between the toe and heel pieces.

* * * * *